(12) United States Patent
Mohr et al.

(10) Patent No.: US 6,794,184 B1
(45) Date of Patent: Sep. 21, 2004

(54) CULTURING DEVICE AND METHOD FOR CULTURING CELLS OR TISSUE COMPONENTS

(75) Inventors: Ulrich Mohr, Hannover (DE); Michaela Aufderheide, Hannover (DE)

(73) Assignee: Ulrich Mohr, Hanover (DE)

( * ) Notice: Subject to any disclaimer, the term of this patent is extended or adjusted under 35 U.S.C. 154(b) by 0 days.

(21) Appl. No.: 09/619,144

(22) Filed: Jul. 19, 2000

Related U.S. Application Data

(63) Continuation of application No. PCT/EP99/00295, filed on Jan. 19, 1999.
(60) Provisional application No. 60/082,817, filed on Apr. 23, 1998.

(30) Foreign Application Priority Data

Jan. 19, 1998 (DE) .......................................... 198 01 763
Jul. 22, 1999 (WO) ............................................ 99/36505

(51) Int. Cl.[7] .............................................. C12M 1/18
(52) U.S. Cl. ..................................... 435/294.1; 435/395
(58) Field of Search ............................. 435/395, 294.1, 435/289.1

(56) References Cited

U.S. PATENT DOCUMENTS

| | | | |
|---|---|---|---|
| 4,370,417 A | | 1/1983 | Hung et al. |
| 4,639,422 A | * | 1/1987 | Geimer et al. .............. 435/286 |
| 4,812,407 A | | 3/1989 | Buchmann et al. |
| 4,974,952 A | * | 12/1990 | Focht ........................... 350/536 |
| 5,175,092 A | * | 12/1992 | Gabriels, Jr. .................. 435/29 |
| 5,424,209 A | * | 6/1995 | Kearney ...................... 435/284 |
| 5,612,188 A | * | 3/1997 | Shuler et al. ................. 435/29 |
| 5,707,869 A | * | 1/1998 | Wolf et al. .................. 435/401 |
| 5,710,043 A | * | 1/1998 | Pay .......................... 435/297.5 |

FOREIGN PATENT DOCUMENTS

| | | | | |
|---|---|---|---|---|
| DE | 42 00 446 A 1 | | 6/1993 | |
| DE | 196 19 114 A 1 | | 12/1996 | |
| GB | 2055397 A | | 3/1981 | |
| GB | 2233769 A | | 1/1991 | |
| GB | 2314343 A | * | 12/1997 | .............. 435/294.1 |
| JP | 57005687 | | 1/1982 | |
| JP | 1211486 A | | 2/1988 | |
| JP | 02119772 | * | 5/1990 | .............. 435/289.1 |
| JP | 4148671 A | | 5/1992 | |
| JP | 8009958 A | | 1/1996 | |
| RU | 734281 B | * | 5/1980 | .............. 435/289.1 |
| SU | 734281 B | * | 5/1980 | .............. 435/289.1 |

* cited by examiner

*Primary Examiner*—James Ketter
(74) *Attorney, Agent, or Firm*—Marshall, Gerstein & Borun LLP

(57) ABSTRACT

A culturing device having one or more culture containers adapted to receive and to discharge a culture medium or nutrient solution is disclosed. The device has a cell culture insert removably received in each of the one or more containers. The device also has at least one supply mechanism for introducing the culture medium into each of the one or more culture containers and for discharging the culture medium from the one or more containers. The device also has at least one level sensor that is arranged to sense a level of the culture medium for the one or more culture containers. The at least one sensor controls the supply mechanism as a function of an output signal from the level sensor that represents the level of the culture medium. The device can carry out a submerged nutrient supply and a basal nutrient supply of cell or tissue cultures in a single culturing device. The device can be adapted to periodically alternate between the submerged and the basal supply condition.

42 Claims, 7 Drawing Sheets

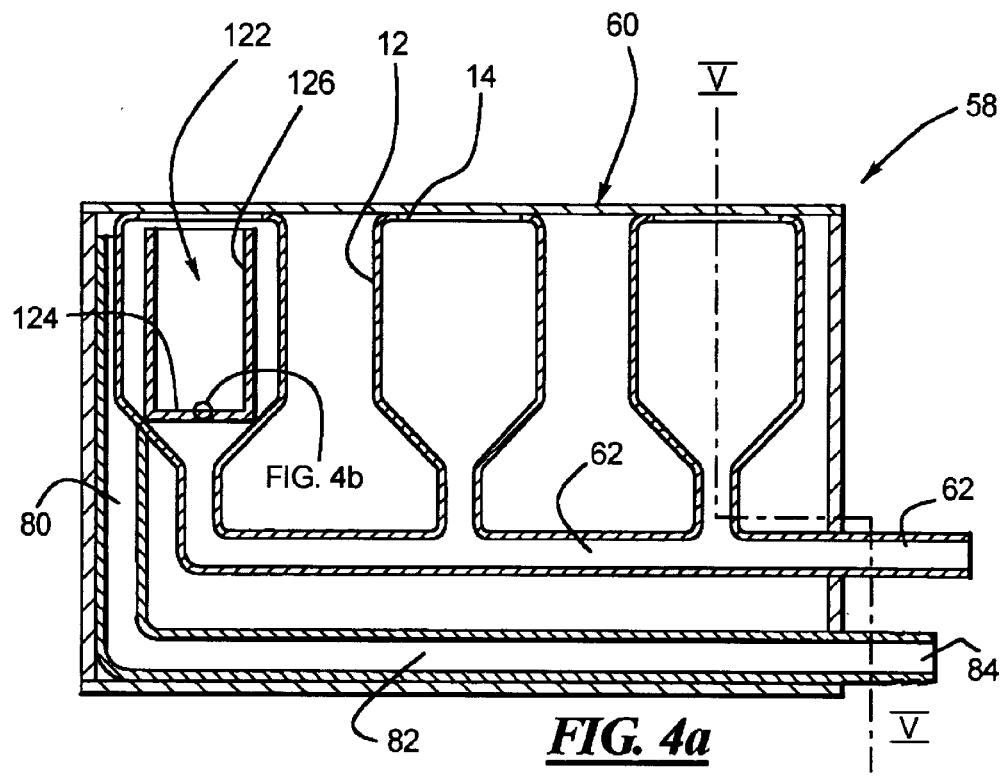
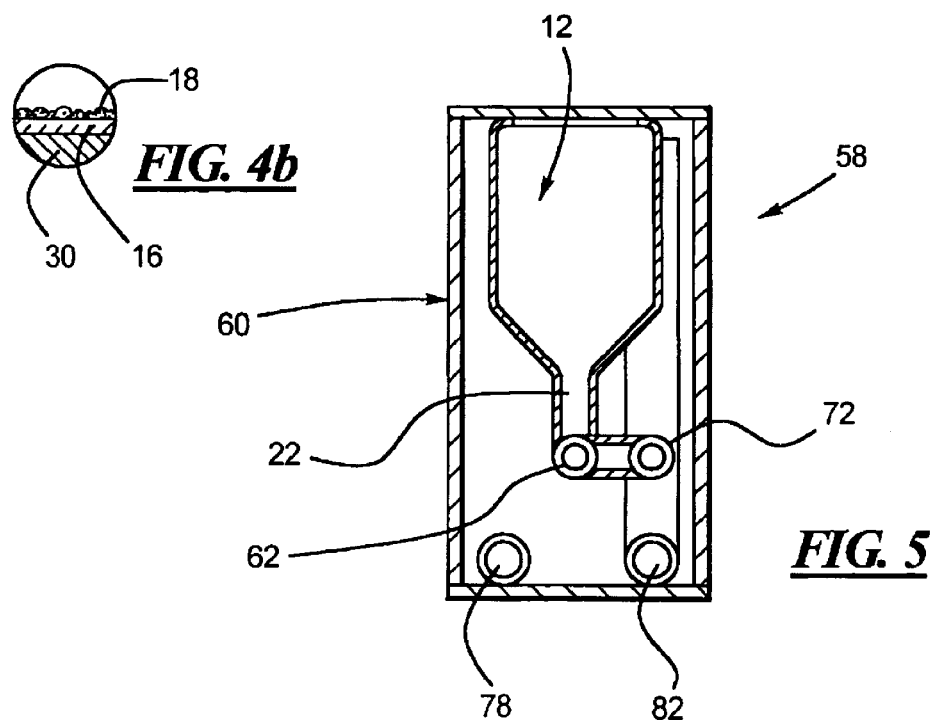

US 6,794,184 B1

CULTURING DEVICE AND METHOD FOR CULTURING CELLS OR TISSUE COMPONENTS

This patent is a continuation of related co-pending international application Serial No. PCT/EP99/00295, filed on Jan. 19, 1999, and published on Jul. 22, 1999 as international publication No. WO 99/36505, and claims priority from U.S. Provisional Application Ser. No. 60/082,817 filed Apr. 23, 1998.

FIELD OF THE INVENTION

The invention is generally related to culturing of cells or tissue components, and more particularly to a culturing device and to a method for changing the level of a culture medium within a culture vessel.

BACKGROUND OF THE INVENTION

Culturing devices are generally known and are used for culturing isolated cells or tissue components in a culturing media. These known culturing devices are limited for use in submerged culture systems. In a submerged system, cultivated cells are supported on the membrane of a cell culture insert and supplied with a culture solution with the appropriate nutrients by layering the solution over the cells. It is not feasible to vary the culture or growth conditions in such a submerged system.

For many experimental studies, such as for example, studies utilizing differentiated ciliary or lung epithelial cells, it would be desirable if the tissue growth conditions could be varied during the studies in order to evaluate and solve special problems. As an example, when using a conventional culturing device, culturing of cells of the respiratory tract cannot be carried out on an air-liquid interface, even if porous membranes are used, which are offered by some companies as so-called transwell systems.

SUMMARY OF THE INVENTION

In a disclosed example of an apparatus constructed in accordance with the teachings of the invention, a culturing device has at least one culture container adapted to receive and to discharge a culture medium. The at least one container has a cell culture insert removably received therein. The device has at least one supply mechanism for introducing the culture medium into the at least one culture container and for discharging the culture medium from the at least one culture container. At least one level sensor cooperates with the at least one culture container to sense a level of the culture medium for the at least one culture container. The sensor controls the supply mechanism as a function of an output signal of the level sensor representing the level of the culture medium such that a submerged culture medium supply condition and a basal culture medium supply condition can both be achieved by the device.

In another disclosed example, the at least one cell culture insert provides a horizontal culture surface within the at least one culture container.

In another disclosed example, the culturing device has at least one pair of discharge lines in fluid communication with the at least one culture container. In another disclosed example, the at least one culture container comprises a plurality of culture containers, and wherein each pair of the discharge lines is associated with a respective one of the individual culture containers. In an alternative disclosed example, the at least one culture container comprises a plurality of culture containers, and wherein at least one pair of the discharge lines is associated with more than one of the individual culture containers.

In another disclosed example, the at least one culture container is positioned so that a culture surface defined by the cell culture insert lies in a common horizontal plane.

In another disclosed example, the at least one culture container comprises a plurality of culture containers, and wherein the plurality of culture containers are connected to a common culture medium supply line.

In a further disclosed example, a supply line is connected to the at least one culture container and communicates with a riser on which the at least one level sensor is carried. In yet another disclosed example, the at least one level sensor is vertically adjustable relative to the riser.

In another disclosed example, the at least one level sensor comprises a plurality of level sensors, and wherein at least one of the plurality of level sensors includes a forked photoelectric barrier.

In another disclosed example, the at least one level sensor continuously measures the culture medium level.

In another disclosed example, the at least one level sensor comprises a plurality of level sensors, and wherein at least one of the plurality of level sensors includes a level switch that responds to a predetermined target level.

In another disclosed example, the culturing device also has an exterior housing and a plurality of discrete modules within the housing. At least one of the at least one culture container is arranged within each of the modules. A culture medium supply distribution system of the device is in fluid communication with a common culture medium supply line and with each of the modules.

In another disclosed example, the supply distribution system has a single connection in fluid communication with the at least one supply mechanism. The single connection is disposed at a lowermost elevation of the supply distribution system.

In another disclosed example, the exterior housing has a plurality of separate connectors each coupled to a withdrawal line of a respective one of the discrete modules.

In another disclosed example, each of the modules includes a discrete temperature-control housing surrounding the at least one of the at least one culture container disposed within the corresponding discrete module. Each temperature-control housing has a temperature-control medium inlet and a temperature-control medium discharge.

In another disclosed example, each temperature-control medium discharge is in fluid communication with an overflow apparatus lying in an upper region of the respective temperature-control housing. The overflow apparatus is positioned diametrically opposite to the temperature-control medium inlet within the respective temperature-control housing.

In another disclosed example, the temperature control medium inlet and discharge of the temperature-control housing of each of the discrete modules is connected in series relative to a flow path of the temperature-control medium.

In another disclosed example, the at least one culture container is disposed within an exterior housing that can provide a sealed environment within an interior of the housing. In another disclosed example, the outer housing has at least one connection for introducing a gaseous medium into the interior of the housing.

In another disclosed example, certain components of the culturing device that must be sterilized are fabricated from materials that can withstand sterilization. In another disclosed example, the sterilizable materials are selected from a group comprising at least one of glass and silicone.

In another disclosed example, the supply mechanism includes a bidirectional pump. In another disclosed example, the bidirectional pump is a peristaltic pump.

In another disclosed example, the at least one sensor comprises a pair of level sensors wherein one of the sensors controls the supply mechanism for the submerged supply condition and the other of the sensors controls the supply mechanism for the basal supply condition.

In another disclosed example, the culturing device also has a programmable controller that can control a culture medium target level transducer in a time-dependent manner. In another disclosed example, the programmable controller can adjust a target level value periodically between at least two values. One is a first level that corresponds to a liquid level that is a predetermined distance above a top side of a culture surface of the cell culture insert of the at least one culture container. The other is a second level that corresponds to a liquid level that is a predetermined distance below the first level.

In another disclosed example of the teachings of the invention, a method for culturing a culture material such as cells and tissue components includes first providing a culturing device having at least one culture container and at least one nutrient solution supply mechanism. A material to be culture is supported within the at least one culture container to expose a quantity of the culture material for culturing. Nutrient solution is then supplied for the culture material to the at least one culture container such that a liquid level of the nutrient solution can be adjusted between at least a submerged culturing level of the nutrient solution and a basal culturing level of the nutrient solution.

In another disclosed example, the method also includes the step of exposing the culture material to at least one other substance during periods where the liquid level is at the basal culturing level, and wherein the at least one other substance is selected from at least one of a solid, gaseous or aerosol-form substance.

In another disclosed example, the step of providing the supply mechanism further includes providing a sensor for sensing the liquid level and a pump controlled by the sensor for supplying the nutrient solution.

In another disclosed example, the step of supplying is carried out with the aid of a programmable controller to automatically adjust the liquid level over a time period.

BRIEF DESCRIPTION OF THE DRAWINGS

FIG. 1b is an enlargement of the device taken from circle 1b in FIG. 1a;

FIG. 2b is an enlargement of the device taken from circle 2b in FIG. 2a;

FIG. 4a is a longitudinal section taken along line IV—IV through a culture module of the culturing device shown in FIG. 3;

FIG. 4b is an enlargement of the device taken from circle 4b in FIG. 4a;

FIG. 5 is an angled transverse section taken along line V—V through the culture module shown in FIG. 4;

DESCRIPTION OF THE PREFERRED EMBODIMENTS

Figure 1A:
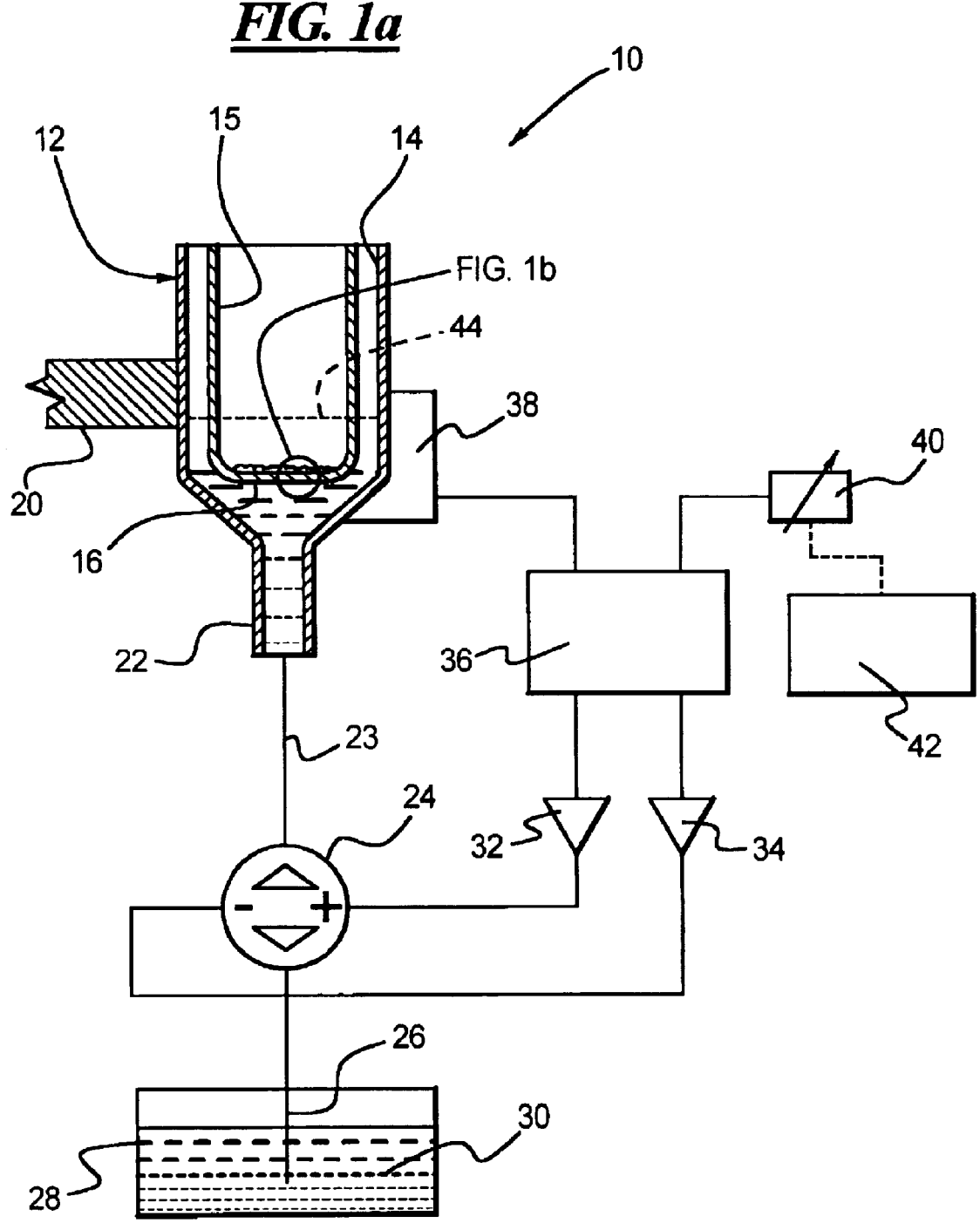
FIG. 1a is a schematic view of a culturing device constructed in accordance with the teachings of the invention and utilizing only one culture container that has a controllable culture medium level.

Referring now to the drawings, FIG. 1a illustrates an entire culture unit 10 having a culture container 12. The illustrated culture unit 10 is generally in the form of an inverted bottle. The upper end of the culture unit 10 defines a circular opening 14.

Figure 1B:
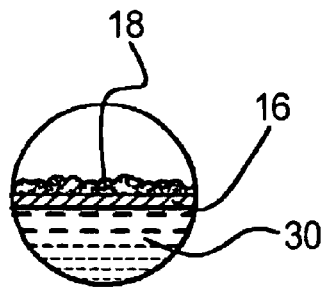

A cell culture insert 15 is placed inside the culture container 12 and is produced from a porous synthetic material, such as for example, polyethylene terephthalate. The cell culture insert 15 has a liquid-permeable carrier structure or membrane 16, which can be produced from the different synthetic materials, depending on the requirements of the cells to be cultured, again such as for example, polyethylene terephthalate. As is shown in FIG. 1b taken from the enlarged portion of FIG. 1a, the membrane 16 supports and carries a cell culture 18.

The culture container 12 is carried by a holding device 20. The structure of the device can vary considerably and is therefore only indicated schematically in FIG. 1a.

A connector 22 on the bottom of the culture container 12 is connected by conventional tubing 23 to the working connection of a bidirectional pump 24. The pump can optionally be a peristaltic pump. The other connection of pump 24 is connected by conventional tubing 26 to the inside of a storage container 28. The storage container contains a reservoir or source of culture liquid 30. The culture liquid contains the particular nutrients which are to be made available to the cell culture 18 for its growth.

Two control terminals of the pump 24 are respectively connected through power amplifiers 32 and 34 to the outputs of an operating circuit 36. The operating circuit 36 produces a signal at a first, a second or neither of its outputs in order to actuate the pump 24. The pump can introduce additional culture liquid from the storage container 28 to the inside of the culture container 12 or can remove culture liquid from the inside of the culture container 12 and return it to the storage container 28. The pump function depends on the output signal of a continuously operating level sensor 38 that is shown as a sensor mounted to the outside surface of the culture container 12. Alternatively, the sensor can also be mounted on the inside surface of the culture container 12. The sensor 38 can be an optical sensor in practice and operate as a function of a target value transducer 40, which is shown as an adjustable resistor. The target value transducer 40 can be adjusted by a programmed controller 42 as indicated in FIG. 1a by a dotted line.

In one practical example discussed herein, the programmed controller 42 switches the target value transducer 40 between two positions. One position of the target value transducer 40 corresponds to a level height of the culture liquid 30 inside the culture container 12. As shown in the drawing, the culture liquid 30 just touches the bottom side of the cell culture insert 15. Under these conditions, the cell culture 18 receives culture liquid only from underneath. This condition is known and is described herein as basal nutrient supply.

The target value transducer 40 is switched to the second position by the programmed controller 42 to correspond to a liquid level shown in FIG. 1a by the dotted line 44. In this position, the liquid level is above the peaks of the cell culture 18. This condition is a submerged nutrient supply system.

Figure 2A:
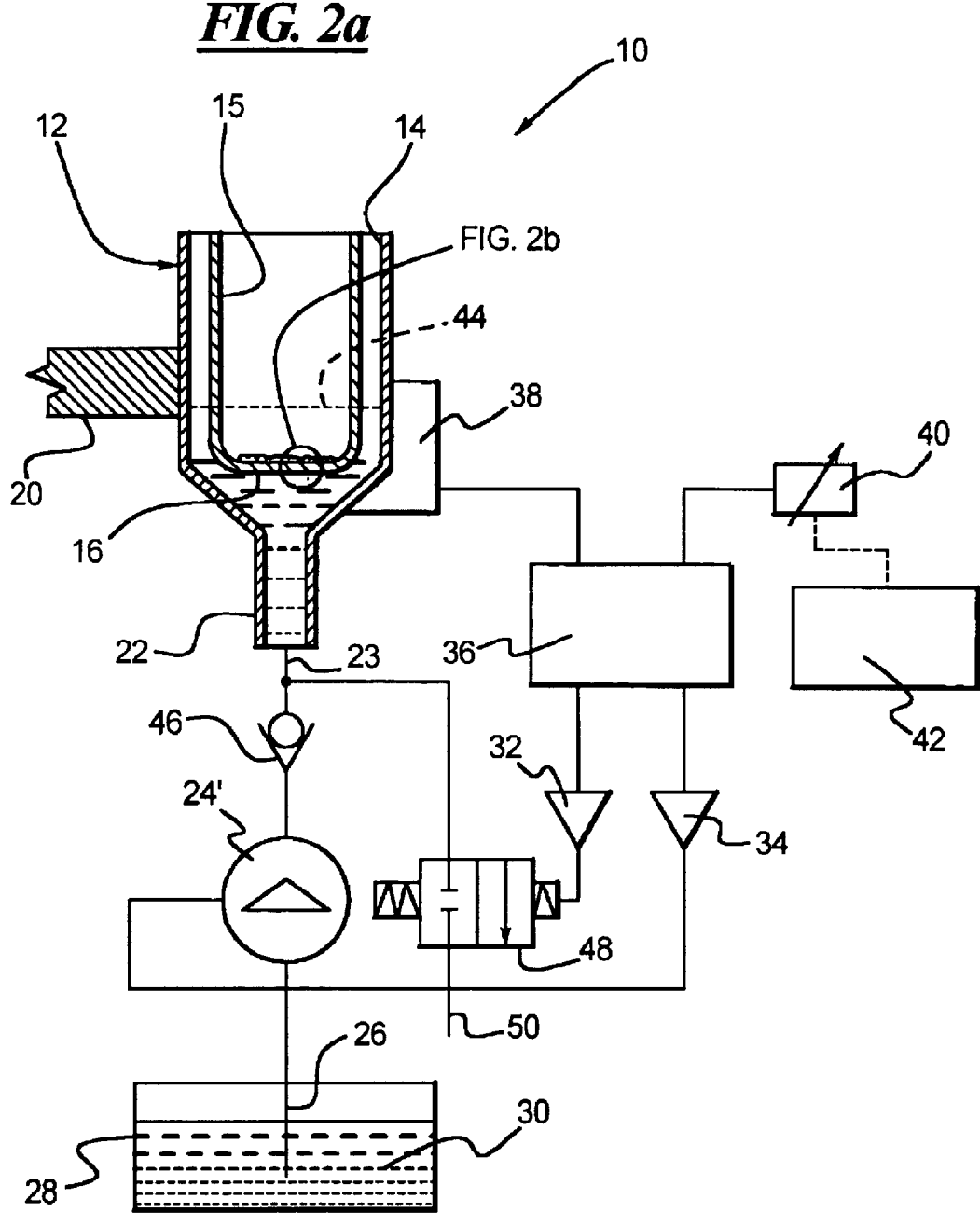
FIG. 2a is a schematic view of another culturing device constructed in accordance with the teachings of the invention.
Figure 2B:
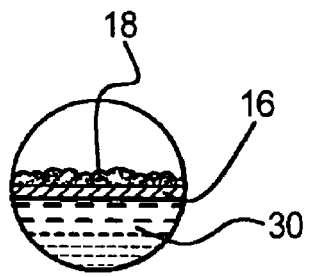

A practical example shown in FIG. 2a corresponds largely to the example shown in FIG. 1a. The corresponding components have the same reference number and will not be explained further in detail.

Instead of the bidirectional pump 24, a unidirectional transport pump 24' is provided and is connected to the connector 22 of the culture container 12 through a check valve 46. Furthermore, a 2/2 magnetic valve 48 connects the culture container 12 to a discharge line 50. The magnetic valve 48 is biased to a closed position with a spring and can be adjusted to an open position. The magnet of the magnetic valve 48 and the pump 24' are again connected to the operating circuit 36 through the power amplifiers 32 and 34, as described above, to form the control circuit.

FIGS. 3 to 7 illustrate a further practical example having a culturing device with a large number of cell cultures being cultivated simultaneously. The culturing device shown in FIGS. 3 to 7 has an outside housing 52 having a lower box-like housing part 54 that in one embodiment is assembled from a plurality of plates. The housing 52 also has a cover 56 that can be tightly placed on the housing to close or seal the device. Three glass bridges 57 extend from the housing cover, along lines 55-1, 55-2 and 55-3, perpendicularly downward, to the upper edge of the culture containers such as the container 12, in order to fix or retain the cell culture inserts 122 within the containers.

Four culture modules 58-1, 58-2, 58-3 and 584 are arranged within the external housing 52. Each of these modules will be identified as a module 58 herein when there is no need to distinguish among the modules.

Each culture module 58 includes a discrete temperature control housing 60 which can also be assembled from a plurality of plates and can each individually support different temperatures or environments. Three culture units 10 are arranged in each of the culture housings 60, as can be seen from the drawing, each including a culture container 12. The connector 22 of each culture container 12 of each culture unit is connected to a common supply line 62 for each module 58.

The supply lines 62 of the various culture modules 58 are each connected through tubing 64 to a corresponding discharge connector 66 of a culture medium distribution system 68. The tubing 64 is shown only schematically in FIG. 3, and can optionally be produced from a material such as silicone. The culture medium distribution system 68 is connected to a supply of culture medium by a supply connector 70. Similar to the practical examples shown in FIGS. 1a and 2a, the supply connector 70 is connected to the discharge of a culture medium pump 24 or 24', also with conventional tubing such as silicone tubing (not shown).

Each of the supply lines 62 has a branch 72 disposed at the end connected to the tubing 64 that lies outside the corresponding temperature-control housing 60. Each branch 72 is connected through a tubing 74 to a corresponding discharge connector 76 of the outer housing 52. In this way, culture liquid 30 can be extracted separately and independently from the various modules 58 for test purposes.

A temperature-control medium, such as for example, temperature-controlled water, is introduced via a temperature-control medium connecting piece 78 into each temperature control housing 60. The temperature-control medium flows equally through the culture containers 12 of a culture module 58. The temperature-control medium is removed through an overflow apparatus 80 that is provided near the corner of the temperature-control housing 60 and is positioned diametrically opposite the connecting piece 78.

An angled section of tubing 82 connects the overflow apparatus 80 to a discharge connector 84 of the temperature-control housing 60. The discharge connector 84 of a given culture module 58 is connected to the connecting piece 78 of the next adjacent culture module 58 with a tubing 86. In this way, the temperature-control medium flows through the temperature-control housings 60 in succession.

The first connecting piece 78-1 is joined to a temperature-control liquid feed connector 88 which is carried by the outer housing 52. The discharge connector 84-1 of a module is connected to the connecting piece 78-2 of the next module through a tubing 86. The last discharge connector 84-2 of the module arrangement is connected through tubing sections 90 and 92 to a temperature-control medium discharge connection 94.

Figure 3:
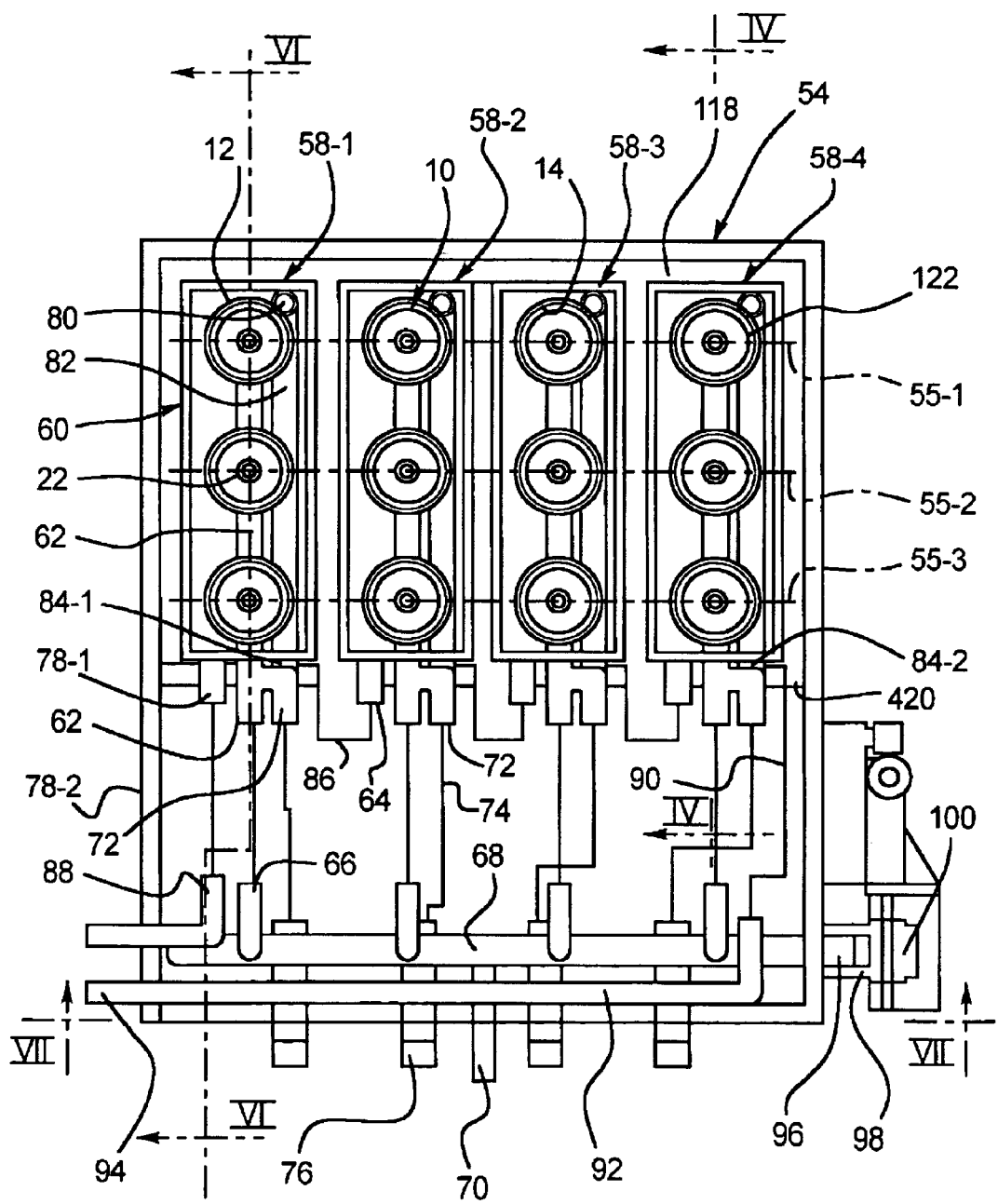
FIG. 3 is a top view of another culturing device constructed in accordance with the teachings of the invention and utilizing a number of culture modules placed parallel to one another, each having a number of culture containers.
Figure 6:
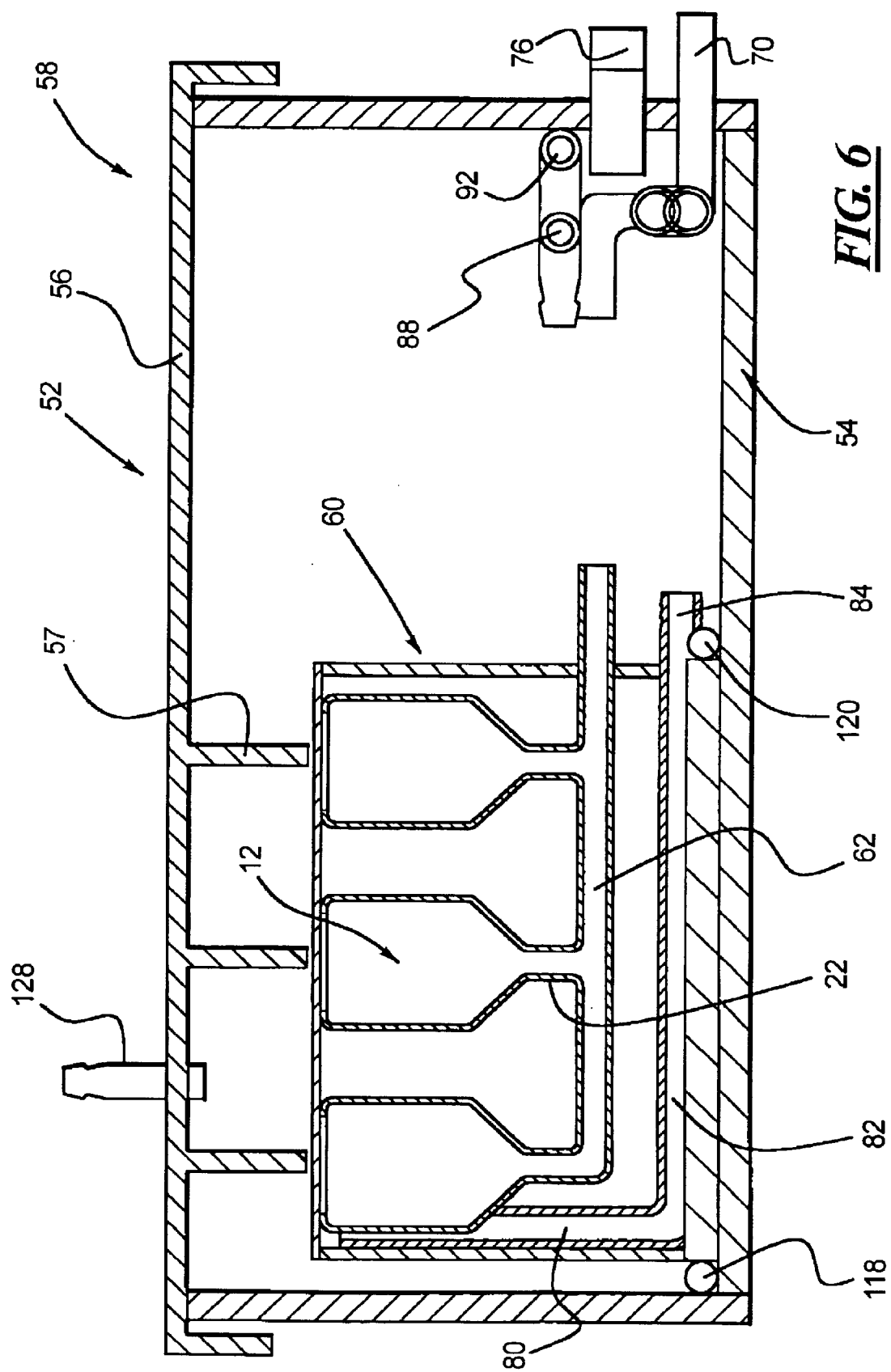
FIG. 6 is a longitudinal section taken along line VI—VI through the culturing device shown in FIG. 3.
Figure 7:
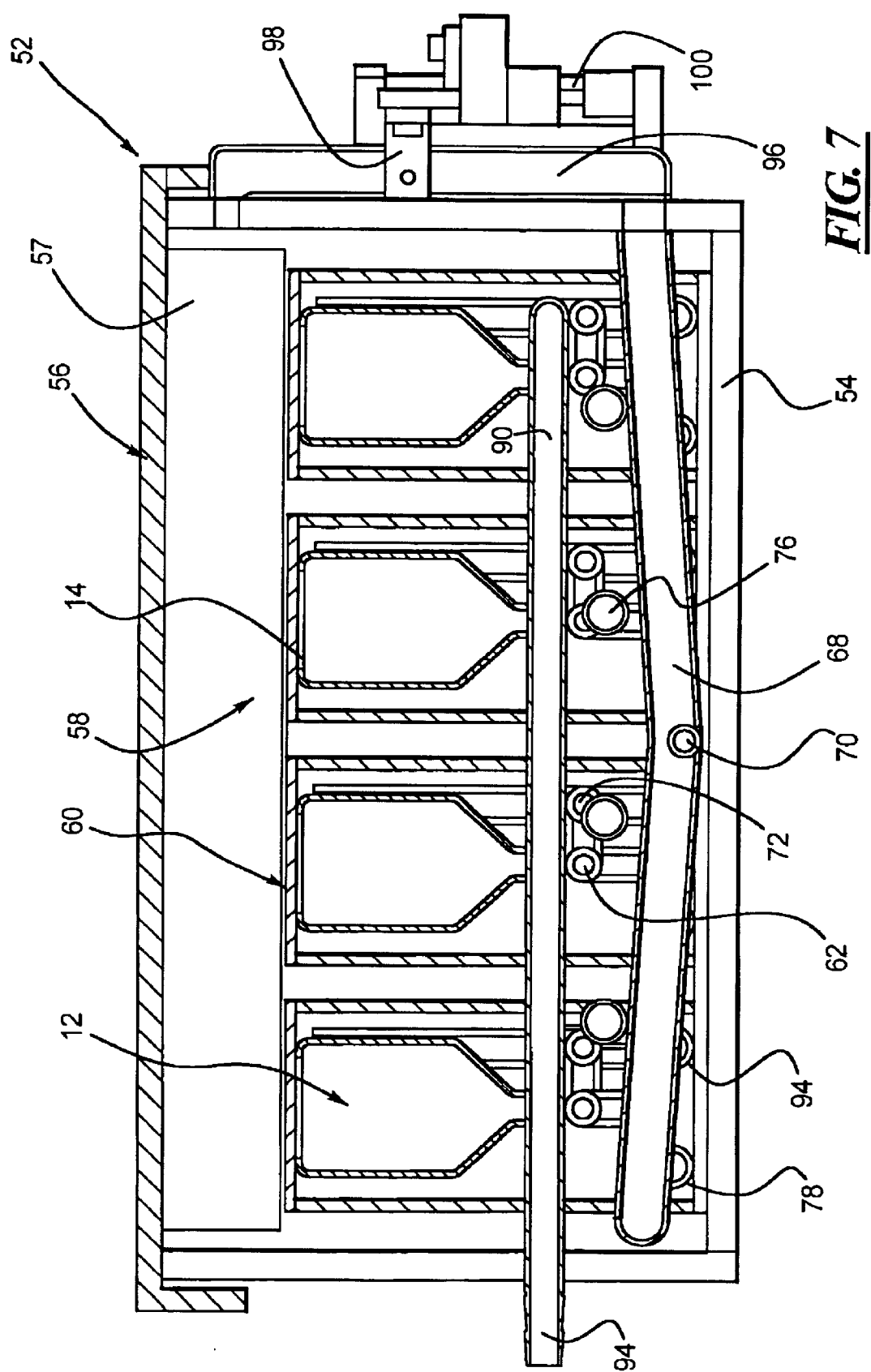
FIG. 7 is a transverse section taken along line VII—VII through the culturing device shown in FIG. 3.

As shown in FIGS. 3 and 7, a riser 96 is connected to the end of the supply line 62. This stands perpendicularly to the plane of the drawing of FIG. 3, as can be seen clearly in FIG. 7. Furthermore, as shown in FIG. 7, the culture medium distributor 68, when viewed from the front, is in the form of a "V" with a wide opening. The supply connector 70 is disposed at the lowest point or elevation of the culture medium distributor 68 and functions both to deliver culture medium and to accept returned culture medium.

Two arms of a forked photoelectric barrier 98 span the outer wall of the riser 96. The forked photoelectric barrier 98 is supported by a holder 100 in such a way that the barrier can be vertically adjusted relative to the riser. The holder 100 extends in the vertical direction parallel to one of the outside plates of outer housing 52.

Figure 8:
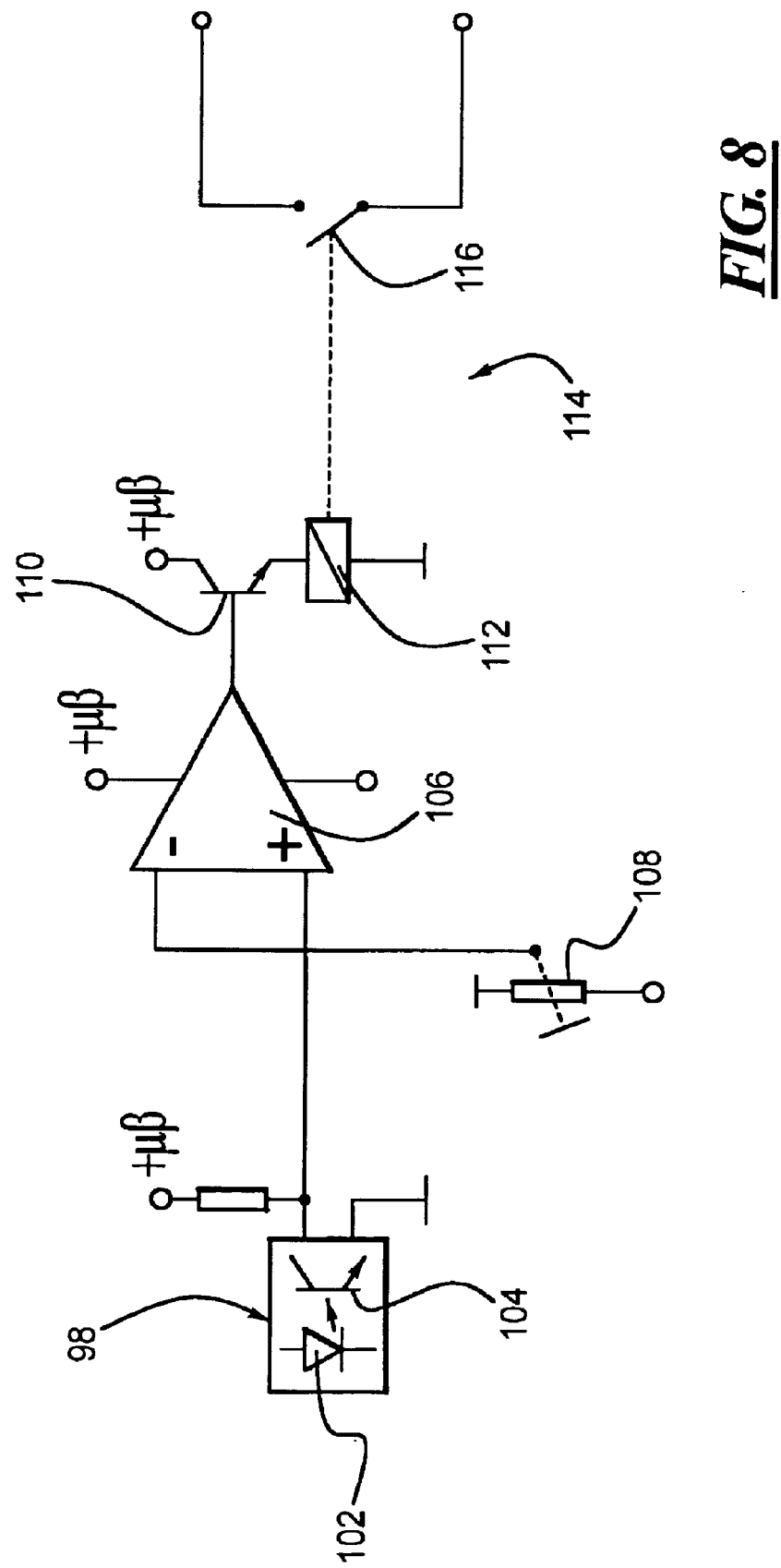
FIG. 8 is a circuit diagram of a level height control which is used in connection with the culturing devices shown in FIGS. 1–7.

An infrared (IR) light source 102 and an IR detector 104, as shown in FIG. 8, can be provided across from one another in the respective arms of the forked photoelectric barrier 98 defining an axis of the barrier. For example, the IR light source can be an IR diode, among other possible devices, and the detector can be an IR-sensitive photo transistor, among other possible devices. Other types of detector devices can be utilized as well that are suitable to perform the functions of the barrier as described below.

The liquid level in the riser 96 corresponds to the liquid level in the various culture containers 12, which are each precisely horizontally aligned. The photoelectric barrier is adjusted to a vertical position that corresponds to a desired liquid height. If the liquid level or column in the riser 96 falls below the axis of the IR photoelectric barrier, the photo transistor 104 provides a signal in the form of electric current to perform a level control function. If the liquid column in the riser 96 rises to the height of the axis of the photoelectric barrier, the output signal of the photo transistor ceases.

A differential amplifier 106 is coupled to the output of the barrier 98 and receives its signals. The amplifier 106 also receives, at a side input, an output signal of a target value transducer 108, which may optionally be implemented by an adjustable resistor. An output signal produced by the differential amplifier 106 activates a switching transistor 110. A relay coil 112 of a reed-relay 114 is then activated via the switching transistor 110. When activated, a reed contact 116 of the reed-relay is closed. The reed contact 116 may optionally be implemented by a potential-free contact and, for example, controls the operation of the pump 24 or 24'. For example, when activated, the reed contact 116 directs the pump to pump additional culture liquid 30.

In one possible implementation of the culturing device, the change from a submerged nutrient supply condition to basal nutrient supply condition can be accomplished. For example, the forked photoelectric barrier 98 can be adjusted downward and excess culture liquid can be manually drained or emptied from the system. A preliminary liquid level can be set to a level significantly below that desired for basal nutrient supply. The liquid level is then increased by the pump under control of the output signal of the forked photoelectric barrier 98, which was previously set to an appropriate level for basal nutrient supply.

One may prefer to periodically switch between the basal and the submerged nutrient supply conditions. In one example of this approach, a second forked photoelectric barrier can be installed. One barrier can be adjusted permanently to detect appropriate liquid levels for basal nutrient supply. The other barrier can then be set to detect liquid levels for submerged nutrient supply. A second control system which corresponds to that shown in FIG. 8, can be provided for operation of the second forked photoelectric barrier. The reed contact 116 of one system can control a bidirectional pump to deliver liquid to increase the culture liquid level when desired. The reed contact 116 of the other system would then control operation of the bidirectional pump for removal of culture liquid.

The various mechanical components of the culturing device described above are preferably made of glass to provide visual access to the interior of the device. The glass must be of sufficient strength and rigidity to withstand the expected rigors of use. Suitable glass components should be capable of sterilization at temperatures of 120° C. without damaging the glass in order to provide a satisfactory germ-free initial state before carrying out the experiments. The various tubing and connections described above are also preferably capable of being sterilized at 120° C. without causing any problems. The tubing elements may optionally be made from a silicone tubing material.

As explained above, only one level sensor is preferably used for controlling the level of the culture liquid in all the various culture containers 12. For this reason, it is necessary to arrange the various culture containers 12 precisely level with one another, so that the surfaces on which the cell cultures grow lie in a common horizontal plane. Two position strips 118 and 120 are provided to accurately position the various culture modules and to lock the culture modules in the outer housing. These strips cooperate with the front edges and/or back edges of the lower plates of the temperature-control housing 60 in order to assist in leveling the housings.

In FIGS. 1a and 2a, the cell culture inserts 15 are shown schematically as being incorporated as part of the container 12 substrates in order to simplify the drawings. However, in practice, the cell culture inserts 15 are preferably not fixed in the culture containers 12, but rather are preferably discrete parts that can be removed from the containers. As indicated in FIG. 4 for a culture container 12, a commercial cell culture insert 122 can be in the shape of a cylindrical beaker with a flat bottom wall 124 and a cylindrical peripheral wall 126. By placing the cell culture inserts 122 into the culture container 12 and securing or supporting them with the aid of the glass bridges 57, the various bottom walls 124 can be assured to lie in a common horizontal plane. The cell culture inserts 122 may optionally be made of a porous synthetic material as can the cell culture inserts 15 in FIG. 1a and 2a.

In the culturing device described above, one can very simply change from submerged to basal nutrient supply of the cell cultures. By changing the temperature of the introduced temperature-control liquid, one can provide additional variation of the growth conditions. A line 128 can also be provided to introduce desired gaseous substances into the outer housing 52, the temperature controlled housings 60, or the individual containers 12. The cell cultures can be exposed to predetermined stressing or therapeutic conditions for desired substances. In the same way, exposure to aerosols can also be performed.

Analogous to treatment with gases and/or aerosols as noted previously, one can also apply or dust particulate active ingredients directly onto the cell cultures to investigate additional desired effects. If one selects particles having an appropriate density relative to the selected culture liquid so that the particles are lighter than the culture liquid, the particles can be lifted off the cell culture when the level of the culture liquid is raised (submerged nutrient supply). On the other hand, when the culture liquid is lowered (basal nutrient supply), the particles again will contact with the cell culture. Such suitable particles are very fine dusts, for example, wood dust or hydrophobic particles, which settle insufficiently or not at all in suspension.

Special attachments can be added to the culture modules to further equip the device for directly applying other substances to the cell culture material. For example, ozone could be directly applied to cells through a separate attachment.

Particles and other complex substances can also be applied to the cells at the air/liquid interface while maintaining the pulsed or periodically varied technique described herein.

Biosensors can also be adapted to cooperate withe the culture modules for either continuous or discontinuous detection of special cell components, such as, for example, calcium, and other cell products. Measuring probes and measuring devices can also be added for continuous or discontinuous measurement of gaseous components, such as $CO_2$ or $NO_2$, or particulate components, such as total particulate matter or TPN, of airborne substances in the atmospheric environment exposed to the cells.

These various possibilities of cell culture are obtained with a simple construction of the apparatus of the culturing device. The culturing devices described above are well suited for the universal use of commercial cell culture inserts. The modular construction of the device permits the culture containers or wells to be adapted or replaced to suit specific desired insert sizes without the need for significantly altering the device.

Performing experiments using the disclosed device is very flexible and three or more parallel experimental batches can be run per module. Although the disclosed device includes three exemplary containers per each of four module, more or fewer culture containers and more or fewer modules can be optionally provided in such a device. When using all modules of the culturing device according to FIGS. 3 to 7, one can run 4 by 3 parallel experimental batches. This permits, for example, determining cell reactions as a function of concentration and/or time.

Some exemplary special cell biological problems that can be investigated and/or solved using the disclosed culturing devices include the following:

1. Treatment of cells with substances such as gases, aerosols, or dusts directly at the air/liquid boundary.
2. Cell interactions by cocultivation of different cell types such as epithelial cells and fibroblasts.
3. Attachment behavior of cells in a system that is supplied with culture liquid in a pulsed manner.
4. Differentiation of cells from cultures upon basal supply of the culture liquid (polarization).
5. Investigation of cilia-carrying cells with basal and/or intermittent supply with culture liquid.
6. Continuous analysis of cell excretion products during the experiment.
7. Intermittent addition of growth-stimulating and growth-inhibiting active ingredients without interruption of the culturing process.
8. Intermittent addition of the substances named under #6 above during exposure of the cells to active or damaging substances.

A culturing device is shown in FIGS. 3 to 7 with its own temperature-control device. However, the device of FIGS. 3 to 7 can be provided without temperature-control, similar to the culturing devices shown in FIGS. 1a and 2a Such a device can simply be placed into a temperature-control cabinet.

Preparation of the culturing device for conducting an experiment is described below. The culturing device in the assembled state but without the cell culture inserts, supply device and level sensor, is sterilized, and particularly is autoclaved at 120° C. in an autoclave for 30 minutes. The device is autoclaved together with other necessary materials, such as pump tubings, tweezers for introducing the cell culture inserts, bottles for holding the culture medium, etc. After the autoclaving, the level sensor is mounted in a clean room workbench, then the culture medium tubing is attached to the pump and the pump speed is adjusted to the intended experimental conditions. Before introducing the cell culture inserts, the culturing device is rinsed by filling the device with the cell-type-specific culture medium and then emptying the device again, after which the used medium is discarded. Then the entire culturing device is filled with the cell-type-specific medium to below the culture containers. The prepared cell culture inserts, which are packed individually and provided by the manufacturer in a sterile form, are introduced to the device with the aid of the tweezers within the clean room workbench. Then the selected program for controlling the pump is started and the culturing device is transferred, if needed, optionally into the temperature-control cabinet. The pump program controls a cycle, which includes the steps of (1) forward-pumping culture medium and culturing time and (2) back-pumping and waiting.

After initialization, the pump carries out its forward pumping function automatically. For this purpose, an adequate pump speed is chosen depending on the cell type and type of culture. The program monitors the output signal of the photocells and terminates the pumping activity as soon as the desired liquid level is reached. Typically, termination of pump activity occurs only after two or several signal detections monitored by the program. This permits avoidance of the detection of erroneous signals which can be produced, for example, by the development of bubbles, and, in the case of a single signal detection, would lead to a premature and undesirable ending of the pumping activity. The subsequent culturing time is preferably selectable and adjustable.

After the culturing time has elapsed, the back pumping or pumping out process of the culture medium is initialized, whereupon, again, the pump speed is preferably selectable and adjustable. The waiting time required for the pumping-off process can be obtained from the selected pumping off speed and the volume of the medium. The cycle as described above and preferably controlled by the program can be repeated once, twice or any desired number of times.

The cell culture inserts can be removed any time in the clean room work-bench. In order to do this, the computer program is stopped. In a case where only a few inserts are removed for analysis, the program can be started again and the above program and cycles repeated.

When the culturing device inserts are completely removed, the entire device can be cleaned. For cleaning, the entire culturing device is rinsed several times with distilled water. The glass parts can also be cleaned with alcohol or other suitable cleaning agents without causing any problems.

The disclosed culturing devices were explained above in conjunction with a particular level sensor. However, it will be evident to those skilled in the art that other level sensors are also suitable and are able to recognize an instantaneous liquid level in the culture container 12 and can provide a corresponding output signal. These include glimmer-controlled sensors, sensors operating on a dielectric principle, sensors with a number of vertically spaced electrodes, other infrared sensors, and ultrasonic sensors.

The culturing devices as described above make a variety of different culturing and exposure conditions possible. The height or level of the culture medium inside the culture vessel can be adjusted so that it lies above the top of the cell culture insert membrane to produce a submerged nutrient supply culture. The level can also be adjusted to a level just contacting the membrane or somewhat within the membrane height in order to produce a basal nutrient supply culture from underneath. Alternately, the liquid level can be intermittently adjusted between a submerged and a basal condition as desired.

Changing from a submerged culture to a basal culture can easily be done by controlling the culture medium supply device. The supply device is controlled to either introduce a predetermined amount of culture medium to the culture vessel or to remove an amount of the medium from the vessel. An output signal from the level sensor corresponds to a specific set level target value to control operation of the supply device. Adjustability of the level of the culture medium in the culture container can be achieved very precisely and simply without reading of marks or similar manual monitoring of equipment. The parts of the apparatus necessary for creating different culturing conditions are simple and inexpensive.

A difference or variance between the submerged and basal nutrient supply can be adjusted very precisely. The various areas of a cell culture carried on a cell culture insert grow under exactly the same conditions. The culture medium located in the individual culture containers can be analyzed during the growth phase. From the composition of the culture medium, one can draw conclusions regarding the growth of cell cultures through their metabolic products. One can grow a large number of cell cultures under exactly the same conditions. The design of such a culturing device for a large number of cell cultures is relatively simple and requires only a relatively small space.

The disclosed devices preferably utilize only one level sensor for the entire device so that no individual cell culture container requires its own sensor. The device can use two sensors, but a second sensor is only necessary where a separate sensor is desired for detecting each of the basal and the submerged liquid levels for the system as described above.

The disclosed device is designed in order to easily determine the culture medium level within the culture container from the outside. Therefore, the containers can have a smooth surface and are free from inserts that would make cleaning the device difficult. The culture containers can also be sterilized simply at high temperatures.

The disclosed device also permits manual adjustment of the target level for the culture medium. The device is equally adaptable to provide for adjusting the target level electronically. The level sensor preferably can measure a large height range of the culture container. The level can also be predetermined by adjusting the level target value signal of the circuit and/or by adjusting the sensor position. A photoelectric sensor for level detection, such as a forked photoelectric barrier, can optionally be used, which are relatively inexpensive and readily available components.

The disclosed culturing device is also well suited for testing multiple cell cultures simultaneously at relatively low cost. The housings, culture containers, inserts and miscellaneous components can be fabricated as mass produced standard components (modules) to further reduce cost and complexity of the device.

The disclosed device also permits removal of culture medium without a residue in the same way from all modules of the culturing device. One can still grow different cell cultures in the different modules. In addition, it is also possible to investigate the progress of growth through the metabolic products for the various cultures (for the various modules).

The disclosed device also permits consistent control of the temperature of various cultures. Without requiring stirring, the device ensures that no temperature gradient develops within the individual constant-temperature containers.

In the disclosed culturing device, the connection between the individual modules of the culturing device is relatively simple between modules. Therefore, the module arrangement can be expanded to include more modules or reduced to include only one or two modules.

In the disclosed culturing device, the interior space of the culture container is separate and sealed from the surrounding atmosphere. The interior space of the entire housing or of individual modules or containers of the device can also be filled with a different gaseous medium to investigate the influence of the gaseous medium on the growth of the cultures.

The disclosed device can provide a satisfactory germ-free initial growth condition, if properly sterilized, for the cell cultures. The disclosed device can be fabricated from a material that is suitable for sterilization and that provides visual inspection of the cell cultures within the interior of the device. A glass material is used in one embodiment and can be selected so that it will not be damaged by or cause damage to the material in the culture container.

In the disclosed culturing device, both the introduction and the discharge of the culture medium can be done utilizing a bidirectional pump and delivery system. The system can be set up to quickly attain a desired target level value and to avoid level oscillations.

In the disclosed culturing device, the cultures can be exposed to stimuli wherein the growth conditions are periodically and easily altered. In addition, the culture can be exposed to substances that are not present in the liquid phase of the nutrient medium, such as gaseous substances or solids that cannot be dispersed in the liquid phase. The device also permits both submerged nutrient supply and basal nutrient supply to be alternated periodically.

The disclosed culture medium in the present device can be controlled via a computer program. This program can be run utilizing virtually any operating system, such as under MS-DOS operating systems. The program can be suitable for controlling all functions of the pumping system. The pumping system can be connected to the computer through a serial interface. The program can be used to detect and to process the output signal of the photocell. The progress of the experiment can be recorded manually, or preferably using the computer program.

Although certain apparatus constructed in accordance with the teachings of the invention have been described herein, the scope of coverage of this patent is not limited thereto. On the contrary, this patent covers all embodiments of the teachings of the invention fairly falling within the scope of the appended claims either literally or under the doctrine of equivalents.

We claim:

1. A culturing device comprising:
   a plurality of culture containers adapted to receive and to discharge a culture medium;
   porous cell culture inserts, one for each of the plurality of culture containers, removably received within the culture containers, said cell culture inserts each providing a horizontal culture surface wherein the plurality of culture containers are positioned so that the horizontal culture surfaces lie in a common horizontal plane; and,
   a supply mechanism for introducing the culture medium into the plurality of culture containers and for discharging the culture medium from the plurality of culture containers;
   wherein a common culture medium supply line connected to the plurality of culture containers communicates with a riser on which at least one level sensor which is vertically adjustable relative to said riser is carried to sense a level of the culture medium for the plurality of culture containers, wherein the sensor controls the supply mechanism as a function of an output signal of the level sensor representing the level of the culture medium such that the device can achieve both a sustained submerged culture medium supply condition and a sustained basal culture medium supply condition, wherein said sustained basal culture medium supply condition allows for exposure of cultured cells on said cell culture insert to gases, aerosols and particulate matter from above and culture medium from below through the porous cell culture insert.

2. A culturing device comprising:
   an exterior housing;
   a plurality of culture containers adapted to receive and discharge a culture medium;
   a plurality of discrete modules within the housing such that there is a plurality of culture containers within each module;
   a porous cell culture insert removably received and providing a horizontal culture surface in each of the culture containers,
   said plurality of culture containers being positioned so that the horizontal culture surfaces lie in a common horizontal plane;
   a supply mechanism for introducing culture medium into each of said culture containers and for discharging the culture medium from each of the culture containers;
   a culture medium distribution system in fluid communication with a culture medium supply line and with each of the modules;
   wherein the exterior housing has a plurality of separate connectors each coupled to a withdrawal line of a respective one of the discrete modules; and wherein each of the discrete modules includes a discrete temperature-control housing surrounding each culture container within the corresponding discrete module, and wherein each temperature control housing has a temperature-control medium inlet and a temperature control medium discharge in fluid communication with an overflow apparatus lying in an upper region of the respective temperature-control housing which overflow apparatus is positioned diametrically opposite to the temperature-control medium inlet within the respective temperature control housing and wherein each of the discrete temperature-control housings can each individually support different temperatures; and a level sensor cooperating with at least one of the culture containers to sense a level of the culture medium for the culture containers, wherein the sensor controls the supply mechanism as a function of an output signal of the level sensor representing the level of the culture medium such that the device can achieve both a sustained submerged culture medium supply condition and a sustained basal culture supply condition, wherein said sustained basal culture medium supply condition allows for exposure of cultured cells on said culture cell insert to gases, aerosols and particulate matter from above and culture medium from below through the porous cell culture insert.

3. A culturing device as defined in claim 2, wherein there are a plurality of culture containers, and wherein each culture container is associated with a pair of discharge lines.

4. A culturing device as defined in claim 3, wherein at least one pair of discharge lines is associated with more than one of the individual culture containers.

5. A culturing device as defined in claim 2, wherein said culture medium supply line is connected to at least one culture container and communicates with a riser on which at least one level sensor is carried.

6. A culturing device as defined in claim 5, wherein the level sensor is vertically adjustable relative to the riser.

7. A culturing device as defined in claim 2, wherein the level sensor comprises a plurality of level sensors, and wherein at least one level sensor includes a forked photoelectric barrier.

8. A culturing device as defined in claim 7, wherein at least one of the level sensors continuously measures the culture medium level.

9. A culturing device as defined in claim 2, wherein there are a plurality of level sensors, and wherein at least one level sensor includes a level switch that responds to a predetermined target level.

10. A culturing device as defined in claim 1, further comprising:

a plurality of culture containers an exterior housing;

a plurality of discrete modules within the housing such that there is a culture container within each module; and a culture medium supply distribution system in fluid communication with a common culture medium supply line and with each of the modules.

11. A culturing device as defined in claim 10, wherein the supply distribution system has a single connection in fluid communication with the supply mechanism, and wherein the single connection is disposed at a lowermost elevation of the supply distribution system.

12. A culturing device as defined in claim 10, wherein the exterior housing has a plurality of separate connectors each coupled to a withdrawal line of a respective one of the discrete modules.

13. A culturing device as defined in claim 10, wherein each of the discrete modules includes a discrete temperature-control housing surrounding each culture container within the corresponding discrete module, and wherein each temperature-control housing has a temperature-control medium inlet and a temperature-control medium discharge.

14. A culturing device as defined in claim 13, wherein each temperature-control medium discharge is in fluid communication with an overflow apparatus lying in an upper region of the respective temperature-control housing, and wherein the overflow apparatus is positioned diametrically opposite to the temperature-control medium inlet within the respective temperature-control housing.

15. A culturing device as defined in claim 14, wherein the temperature control medium inlet and discharge of the temperature-control housing of each of the discrete modules is connected in series relative to a flow path of the temperature-control medium.

16. A culturing device as defined in claim 2, wherein the plurality of discrete modules is disposed within an exterior housing that can provide a sealed environment within an interior of the housing.

17. A culturing device as defined in claim 16, wherein the exterior housing has a connection for introducing a gaseous medium into the interior of the housing.

18. A culturing device as described in claim 2, wherein certain components of the culturing device that must be sterilized are fabricated from materials that can withstand sterilization.

19. A culturing device as defined in claim 18, wherein the sterilizable materials are selected from a group consisting of glass and silicone.

20. A culturing device as defined in claim 2, wherein the supply mechanism includes a bidirectional pump.

21. A culturing device as described in claim 20, wherein the bidirectional pump is a peristaltic pump.

22. A culturing device as defined in claim 2, wherein there is a pair of level sensors wherein one of the sensors controls the supply mechanism for the submerged supply condition and the other sensor controls the supply mechanism for the basal supply condition.

23. A culturing device as defined in claim 2, further comprising:

a programmable controller that can control a culture medium target level transducer in a time-dependent manner.

24. A culturing device as defined in claim 23, wherein the programmable controller can adjust a target level value periodically between at least two level values, a first level value corresponding to a liquid level that is a predetermined distance above a top side of a culture surface of the cell culture insert in the culture container, and a second level value corresponding to a liquid level that is a predetermined distance below the first level.

25. A culturing device as defined in claim 1, wherein there are a plurality of culture containers, and wherein each culture container is associated with a pair of discharge lines.

26. A culturing device as defined in claim 1, wherein the level sensor is vertically adjustable relative to the riser.

27. A culturing device as defined in claim 1, wherein the level sensor comprises a plurality of level sensors, and wherein at least one level sensor includes a forked photoelectric barrier.

28. A culturing device as defined in claim 27, wherein at least one of the level sensors continuously measures the culture medium level.

29. A culturing device as defines in claim 1, wherein there are a plurality of level sensors, and wherein at least one level sensor includes a level switch that responds to a predetermined target level.

30. A culturing device as defined in claim 1, wherein the supply distribution system has a single connection in fluid communication with the supply mechanism, and wherein the single connection is disposed at a lowermost elevation of the supply distribution system.

31. A culturing device as defined in claim 1, wherein the culture container is disposed within an exterior housing that can provide a sealed environment within an interior of the housing.

32. A culturing device as defined in claim 31, wherein the outer housing has a connection for introducing a gaseous medium into the interior of the housing.

33. A culturing device as described in claim 1, wherein certain components of the culturing device that must be sterilized are fabricated from materials that can withstand sterilization.

34. A culturing device as defined in claim 33, wherein the sterilizable materials are selected from a group consisting of glass and silicone.

35. A culturing device as defined in claim 1, wherein the supply mechanism includes a bidirectional pump.

36. A culturing device as described in claim 35, wherein the bidirectional pump is a peristaltic pump.

37. A culturing device as defined in claim 1, wherein there is a pair of level sensors wherein one of the sensors controls the supply mechanism for the submerged supply condition and the other sensor controls the supply mechanism for the basal supply condition.

38. A culturing device as defined in claim 1, further comprising:
    a programmable controller that can control a culture medium target level transducer in a time-dependent manner.

39. A culturing device as defined in claim 38, wherein the programmable controller can adjust a target level value periodically between at least two level values, a first level value corresponding to a liquid level that is a predetermined distance above a top side of a culture surface of the cell culture insert in the culture container, and a second level value corresponding to a liquid level that is a predetermined distance below the first level.

40. A culturing device as defined in claim 2, wherein the exterior housing has a plurality of separate connectors each coupled to a withdrawal line of a respective one of the discrete modules.

41. A culturing device as defined in claim 2, wherein each temperature-control medium discharge is in fluid communication with an overflow apparatus lying in an upper region of the respective temperature-control housing, and wherein the overflow apparatus is positioned diametrically opposite to the temperature-control medium inlet within the respective temperature-control housing.

42. A culturing device as defined in claim 2, wherein the temperature control medium inlet and discharge of the temperature-control housing of each of the discrete modules is connected in series relative to a flow path of the temperature-control medium.

* * * * *